(12) United States Patent
Costello et al.

(10) Patent No.: US 9,796,691 B2
(45) Date of Patent: Oct. 24, 2017

(54) PARTIALLY FLUORINATED KETONES AND METHODS OF MAKING AND USING THE SAME

(75) Inventors: Michael G. Costello, Afton, MN (US); Michael J. Bulinski, Houlton, WI (US); Richard M. Flynn, Mahtomedi, MN (US)

(73) Assignee: 3M INNOVATIVE PROPERTIES, St. Paul, MN (US)

( * ) Notice: Subject to any disclaimer, the term of this patent is extended or adjusted under 35 U.S.C. 154(b) by 498 days.

(21) Appl. No.: 14/123,788

(22) PCT Filed: May 22, 2012

(86) PCT No.: PCT/US2012/038960
§ 371 (c)(1),
(2), (4) Date: Dec. 4, 2013

(87) PCT Pub. No.: WO2012/170196
PCT Pub. Date: Dec. 13, 2012

(65) Prior Publication Data
US 2014/0130713 A1 May 15, 2014

Related U.S. Application Data

(60) Provisional application No. 61/495,633, filed on Jun. 10, 2011.

(51) Int. Cl.
| | | |
|---|---|---|
| *C09B 67/00* | (2006.01) |
| *C07D 265/28* | (2006.01) |
| *C07C 49/175* | (2006.01) |
| *C07D 295/084* | (2006.01) |
| *C07D 307/12* | (2006.01) |
| *C09D 7/12* | (2006.01) |

(52) U.S. Cl.
CPC .......... *C07D 265/28* (2013.01); *C07C 49/175* (2013.01); *C07D 295/084* (2013.01); *C07D 307/12* (2013.01); *C09D 7/1233* (2013.01)

(58) Field of Classification Search
CPC .......................... C07D 7/1233; C07D 265/28; C07D 295/084; C07D 307/12; C07C 49/175
USPC ................................... 106/287.21
See application file for complete search history.

(56) References Cited

U.S. PATENT DOCUMENTS

| 2,713,593 A | 7/1955 | Brice et al. |
| 2,988,537 A | 6/1961 | Wiley |
| 3,903,012 A | 9/1975 | Brandreth |
| 4,169,807 A | 10/1979 | Zuber |
| 5,125,089 A | 6/1992 | McCambridge |
| 5,125,978 A | 6/1992 | Flynn et al. |
| 5,182,342 A | 1/1993 | Feiring et al. |
| 5,210,106 A | 5/1993 | Dams et al. |
| 5,539,008 A | 7/1996 | Dams et al. |
| 5,925,611 A | 7/1999 | Flynn et al. |
| 6,080,448 A | 6/2000 | Leiner et al. |
| RE37,119 E | 4/2001 | Sherwood |
| 6,374,907 B1 | 4/2002 | Tousignant et al. |
| 6,399,729 B1 | 6/2002 | Farnham et al. |
| 6,759,374 B2 | 7/2004 | Milbrath et al. |
| 2008/0139683 A1 | 6/2008 | Flynn et al. |

FOREIGN PATENT DOCUMENTS

| WO | WO 01/46116 | 6/2001 |
| WO | WO 2007-075804 | 7/2007 |
| WO | WO 2008-070606 | 6/2008 |
| WO | WO 2011/119421 | 9/2011 |

OTHER PUBLICATIONS

"Synthesis of Fluoro Nitro Ethers" J. Org. Chem, 1990, vol. 55, p. 3562-3565.
Grenfell, M.W.; "40576 Hydrofluoroethers as Fluoromonomer Reaction Media", Research Disclosures; Jan. 1998, 3M Chemicals; pp. 81-82.
Banks, R.E. et al.; "Chapter 1—Electrochemical Fluorination (Simons Process) as a Route to Perfluorinated Organic Compounds of Industrial Interest"; Preparation, Properties, and Industrial Applications of Organofluorine Compounds; (1982); pp. 19-43.

*Primary Examiner* — Alexander Polyansky
(74) *Attorney, Agent, or Firm* — Adam Bramwell; Stephen F. Wolf

(57) ABSTRACT

Partially fluorinated ketones are provided that include a terminal alkyl group having from 1 to 6 carbon atoms bonded to a carbonyl group and a hydrofluoroether moiety having from 2 to 4 carbon atoms that contains at least one hydrogen substituent. The hydrofluoroether moiety is bonded to the carbonyl group with a carbon-carbon bond. The ether oxygen is bonded to a carbon atom that is at least two carbon atoms removed from the carbonyl group. Additionally, a fluorinated alkyl group having from 1 to 10 carbon atoms is bonded to the ether oxygen of the hydrofluoroether moiety. These partially fluorinated ketones can be used in a wide variety of electronics applications.

13 Claims, No Drawings

PARTIALLY FLUORINATED KETONES AND METHODS OF MAKING AND USING THE SAME

FIELD

This disclosure relates to partially fluorinated ketone compounds and processes for making and using the same.

BACKGROUND

Presently various fluids are used for heat transfer, cleaning solvents, deposition solvents and other purposes in the electronics industry. The suitability of a fluid depends upon the application process. For example, some electronic applications require fluids which are inert, have a high dielectric strength, have low toxicity, have good environmental properties, and have good heat transfer properties over a wide temperature range. Other applications require precise temperature control and thus the heat-transfer fluid is required to be a single phase over the entire process temperature range and the heat-transfer fluid properties are required to be predictable, i.e., the composition remains relatively constant so that the viscosity, boiling point, etc. can be predicted so that a precise temperature can be maintained and so that the equipment can be appropriately designed.

Perfluorocarbons, perfluoropolyethers, and some hydrofluoroethers have been used for heat transfer and other purposes in the electronic industry. Perfluorocarbons (PFCs) can have high dielectric strength and high resistivity. PFCs can be non-flammable and are generally mechanically compatible with materials of construction, exhibiting limited solvency. Additionally, PFCs generally exhibit low toxicity and good operator friendliness. PFCs can be manufactured in such a way as to yield a product that has a narrow molecular weight distribution. They can exhibit one important disadvantage, however, and that is a long atmospheric lifetime which can give rise to a high global warming potential (GWP).

Perfluoropolyethers (PFPEs) exhibit many of the same advantageous attributes described for PFCs. They also have the same major disadvantage, i.e., a long atmospheric lifetime which can give rise to a high global warming potential (GWP). In addition, the methods developed for manufacturing these materials can yield products that are not of consistent molecular weight and thus can be subject to performance variability.

Hydrofluoropolyethers (HFPEs), a class of hydrofluoroethers (HFEs), can exhibit some of the same advantageous attributes of PFCs, but differ greatly in two areas. They can exhibit markedly lower environmental persistence, yielding atmospheric lifetimes on the order of decades rather than millennia which can give rise to a lower, though still relatively high, global warming potential. However, some of the HFPEs taught as heat-transfer fluids can be a mixture of components of widely disparate molecular weight. Thus, their physical properties may change over time which makes it difficult to predict performance.

SUMMARY

The need exists for electronic fluids that are inert, have high dielectric strength, low electrical conductivity, chemical inertness, thermal stability and effective heat transfer, are liquid over a wide temperature range, have good heat-transfer properties over a wide range of temperatures and also have an acceptable environmental profile including a relatively short atmospheric lifetime and relatively low global warming potential (GWP). The need exists for electronic fluids that can be low GWP alternatives to many applications where perfluorocarbons, perfluoropolyethers, and hydrofluoroethers are currently used. The provided partially fluorinated ketones are a new and unique class of compounds which can find utility in the electronics industry as low GWP alternatives to currently used materials.

In one aspect, a partially fluorinated ketone compound is provided that includes a terminal alkyl group having between 1 to 6 carbon atoms bonded to a carbonyl group to which is bonded a partially fluorinated hydrocarbon moiety, wherein the partially fluorinated hydrocarbon moiety has from 2 to 4 carbon atoms and contains at least one hydrogen substituent; an ether oxygen bonded to a carbon atom that is at least two carbons removed from the carbonyl group; and a fluorinated alkyl group, having from 1 to 10 carbon atoms, bonded to the ether oxygen of the partially fluorinated hydrocarbon moiety, wherein the fluorinated alkyl group may contain at least one catenated oxygen or nitrogen atom. The terminal alkyl group can be linear, branched, cyclic or a combination thereof. In some embodiments, the terminal alkyl group can be ethyl or methyl. Additionally, at least one of the terminal alkyl group or the fluorinated alkyl group can include at least one catenated nitrogen or oxygen atom. The fluorinated alkyl group can be perfluorinated. In some embodiments the provided partially fluorinated ketone compounds can include two terminal alkyl groups, two partially fluorinated hydrocarbon moieties, and a fluorinated alkylene group wherein both partially fluorinated hydrocarbon moieties are directly bonded to the fluorinated alkylene group and wherein each partially fluorinated hydrocarbon moiety is bonded to one terminal alkyl group.

In another aspect, a partially fluorinated ketone is provided having the formula:

$R_H C(=O)CF_2CFHOR_f$, or

$R_H^1 C(=O)CF_2CFHOR_fOCFHCF_2C(=O)R_H^2$ wherein each $R_H$, $R_H^1$, and $R_H^2$ is, independently, an alkyl group having from 1 to 6 carbon atoms, and wherein $R_f$ is a fluorinated alkyl moiety having from 1 to 10 carbon atoms which can include at least one catenated nitrogen or oxygen atom. Each $R_H$, $R_H^1$, and $R_H^2$ can be, independently, linear, branched, cyclic, or a combination thereof. In some embodiments, $R_f$ can be perfluorinated. $R_H$, $R_H^1$, and $R_H^2$ can include at least one catenated nitrogen or oxygen atom.

In another aspect, a process is provided for removing a contaminant from an article that includes contacting the article with at least one provided partially fluorinated ketone compound.

In another aspect, a process is provided for preparing a foamed plastic that includes vaporizing a blowing agent mixture in the presence of at least one foamable polymer or the precursors of at least one foamable polymer, said blowing agent mixture comprising at least one provided partially fluorinated ketone compound.

In another aspect, a process for transferring heat is provided that includes transferring heat between a heat source and a heat sink through the use of a heat transfer agent that comprises at least provided one partially fluorinated ketone compound.

In another aspect, a process for depositing a coating on a substrate is provided that includes applying to at least a portion of at least one surface of said substrate a composition comprising (a) a solvent composition comprising at least one provided partially fluorinated ketone compound and (b) at least one coating material that is soluble or dispersible in said solvent composition.

In another aspect, a polymerization process is provided that includes polymerizing at least one monomer in the presence of at least one polymerization initiator in the presence of at least one provided partially fluorinated ketone compound.

In yet another aspect, a method of preparing partially fluorinated ketones is provided that includes reacting an alkyl aldehyde having from 2 to 6 carbon atoms with a perfluorinated vinyl ether using a free-radical initiator to form at least one partially fluorinated ketone, wherein the partially fluorinated ketone comprises a partially fluorinated hydrocarbon moiety, having from 2 to 4 carbon atoms, containing at least one hydrogen substituent, bonded to the carbonyl group with a carbon-carbon bond, and an ether oxygen that is distal to the carbonyl group; and a fluorinated alkyl group, having from 1 to 6 carbon atoms, bonded to the ether oxygen of the partially fluorinated hydrocarbon moiety, and wherein the fluorinated alkyl group may contain at least one catenated oxygen or nitrogen atom.

In the present disclosure,

"catenated heteroatom" refers to an atom other than carbon (for example, oxygen or nitrogen) that is bonded to carbon atoms in a carbon chain so as to form a carbon-heteroatom-carbon chain;

"ether oxygen bonded to a carbon atom that is at least two carbons removed from the carbonyl group" refers to a structure that has a partially fluorinated alkylene moiety that includes a carbon chain of at least two carbon atoms between the ether oxygen and the carbonyl group;

"fluoro-" (for example, in reference to a group or moiety, such as in the case of "fluoroalkylene" or "fluoroalkyl" or "fluorocarbon") or "fluorinated" refers to only partially fluorinated such that there is at least one carbon-bonded hydrogen atom;

"fluorochemical" refers to "fluorinated" or "perfluorinated"; and

"perfluoro-" (for example, in reference to a group or moiety, such as in the case of "perfluoroalkylene" or "perfluoroalkyl" or "perfluorocarbon") or "perfluorinated" refers to completely fluorinated such that, except as may be otherwise indicated, there are no carbon-bonded hydrogen atoms replaceable with fluorine.

The provided partially fluorinated ketones can be used in a number of different applications including, for example, use as a solvent in coating deposition, as a cleaning or drying fluid, as a dry cleaning fluid, as a polymerization medium, as a document preservation medium, as a heat transfer agent, as a cell size regulator for use in foam blowing and as a metal working agent in the cutting or forming of metals. At least some of the partially fluorinated ketones boil above 100° C. yet also exhibit surprisingly good low temperature viscosity characteristics. Thus, at least some embodiments of the invention meet the above-described, ongoing need for partially fluorinated ketones that can meet the performance requirements of a variety of different applications (as well as the need for efficient and cost-effective processes for their preparation).

The above summary is not intended to describe each disclosed embodiment of every implementation of the present invention. The detailed description which follows more particularly exemplifies illustrative embodiments.

DETAILED DESCRIPTION

In the following description, reference is made to several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about" Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Partially fluorinated ketones are provided that include a terminal alkyl group having between 1 to 6 carbon atoms bonded to a carbonyl group to which is bonded a partially fluorinated hydrocarbon moiety having from 2 to 4 carbon atoms and containing at least one hydrogen substituent. The provided partially fluorinated ketones also include an ether oxygen bonded to a carbon atom that is at least two carbons removed from the carbonyl group. The provided partially fluorinated ketones also include a fluorinated alkyl group, having from 1 to 10 carbon atoms, bonded to the ether oxygen of the partially fluorinated hydrocarbon moiety. The fluorinated alkyl group may contain at least one catenated oxygen or nitrogen atom.

The terminal alkyl group can be linear, branched, cyclic, or a combination thereof. In some embodiments, the terminal alkyl group can be ethyl or methyl. The partially fluorinated hydrocarbon moiety can comprise (—$CF_2$—$CFH$—) with the (—$CF_2$—) bonded to the carbonyl group. In some embodiments, the fluorinated alkyl group can be perfluorinated and can comprise a terminal group.

Exemplary partially fluorinated ketone compounds include $C_3F_7OCFHCF_2C(O)CH_3$, $C_3F_7OCF(CF_3)CF_2OCFHCF_2C(O)CH_3$, $CF_3OCFHCF_2C(O)CH_3$, $C_4F_9OCFHCF_2C(O)CH_3$, $CF_3OC_3F_6OCFHCF_2C(O)CH_3$, $C_2F_5OCFHCF_2C(O)CH_3$, $(CF_3)_2CFCF_2OCFHCF_2C(O)CH_3$, $C_5F_{11}OCFHCF_2C(O)CH_3$, $HCF_2CF_2CF_2OCFHCF_2C(O)CH_3$, $CH_3OCF_2CF_2CF_2OCFHCF_2C(O)CH_3$,

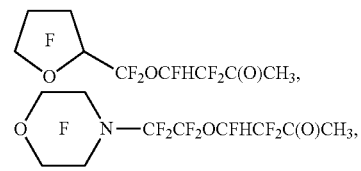

$CH_3C(O)CF_2CFHOC_4F_8OCFHCF_2C(O)CH_3$, $C_3F_7OCFHCF_2C(O)CH_2CH_3$, $C_3F_7OCFHCF_2C(O)CH_2CH_2CH_3$, $C_3F_7OCFHCF_2C(O)CH(CH_3)_2$, $C_4F_9OCFHCF_2C(O)CH_2CH_3$, $C_4F_9OCFHCF_2C(O)CH_2CH_2CH_3$, $C_4F_9OCFHCF_2C(O)CH(CH_3)_2$, $CF_3OC_3F_6OCFHCF_2C(O)CH_2CH_3$, $CF_3OC_3F_6OCFHCF_2C(O)CH_2CH_2CH_3$, $CF_3OC_3F_6OCFHCF_2C(O)CH(CH_3)_2$, $CF_3OCFHCF_2C(O)CH_2CH_3$, $CF_3OCFHCF_2C(O)CH_2CH_2CH_3$, $CF_3OCFHCF_2C(O)CH(CH_3)_2$, $C_3F_7OCF(CF_3)CF_2OCFHCF_2C(O)CH_2CH_3$, $C_3F_7OCF(CF_3)CF_2OCFHCF_2C(O)CH_2CH_2CH_3$, $C_3F_7OCF(CF_3)CF_2OCFHCF_2C(O)CH(CH_3)_2$, $CH_3CH_2C(O)CCF2CFHOC_4F_8OCFHCF_2C(O)CH_2CH_3$, $CH_3CH_2CH_2C$ (O)CF$_2$CFHOC$_4$F$_8$OCFHCF$_2$C(O)CH$_2$CH$_2$CH$_3$, (CH$_3$)$_2$CH(O)CCF$_2$CFHOC$_4$F$_8$OCFHCF$_2$C(O)CH(CH$_3$)$_2$,

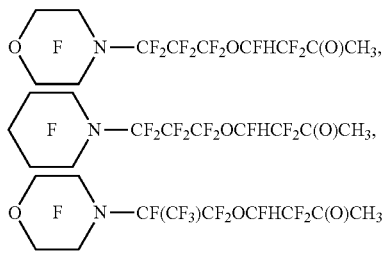

and mixtures thereof.

The provided partially fluorinated ketone compounds can be prepared by the free-radical addition of an alkyl aldehyde with fluoro- or perfluorovinyl ethers. The aldehydes can have an alkyl group that contains from 1 to 6 carbon atoms. The aldehydes have the structure, R—C(O)—H, where R is the alkyl group. Typically, the alkyl group is a straight chained or branched alkyl group such as, for example, methyl, ethyl, propyl or iso-propyl. In some embodiments, the alkyl group can have at least one catenated oxygen or nitrogen atom.

Typically, the alkyl aldehyde and the fluoro- or perfluorovinyl ethers are placed in a pressure reactor such as a Parr reactor along with a free-radical initiator that works at the appropriate reaction temperature for the desired reaction. Typical free-radical initiators include peroxides and azo compounds. Typical peroxides include diacyl peroxides, dialkyl peroxydicarbonates, t-alkyl peroxyesters, di-(t-alkyl) peroxyketals, and di-t-alkyl peroxides. Particularly useful are initiators that have initiating temperatures between about 65° C. and 135° C. These include peroxides under the trade designation LUPEROX (available from Arkema, Inc, Philadelphia, Pa.) or under the trade designations CUROAT, CUROX (available from United Initiators, Pullach Germany). Exemplary organic peroxides include 1,1-di(t-amylperoxy)cyclohexane, 1,1-di(t-butylperoxy)3,3,5-trimethyl cyclohexane, t-amyl peroxy-2-ethyl hexanoate, benzoyl peroxide, t-amyl peroxybenzoate, t-butyl peroxyacetate, t-butyl peroxybenzoate ethyl 3,3-di-(t-amylperoxy)butyrate, ethyl 3,3-di(t-butylperoxy)butyrate, and dicumyl peroxide. Azo initiators include compounds available under the trade designation PERCARBAMID (United Initiators) and include materials such as carbamide peroxide. Additional azo initiators include azobisisobutyronitrile (AIBN) and 2,2'-azodi(2-methylbutyronitrile).

Fluoro- and perfluorovinyl ethers that are useful in carrying out the process of preparation of the provided partially fluorinated ketones include those that possess a terminal perfluorovinyl group. Such fluoro- and perfluorovinyl ethers, which optionally, can further contain one or more catenated heteroatoms (in addition to the ether oxygen of the fluoro- and perfluorovinyl ethers), can be prepared by the reaction of a fluorochemical acid fluoride or a fluorochemical ketone with hexafluoropropylene oxide (HFPO) to form an intermediate branched acid fluoride adduct. This adduct can then be reacted with a base to form an intermediate carboxylic acid salt, which can then be decarboxylated at elevated temperature (optionally, in the presence of an inert solvent). Some perfluorovinyl ethers (for example, perfluorovinyl ethers such as C$_3$F$_7$OCF=CF$_2$, C$_3$F$_7$OCF(CF$_3$)CF$_2$OCF=CF$_2$, and CF$_3$OCF=CF$_2$) are also commercially available (for example, from Synquest Laboratories, Alachua, Fla. or from Apollo Scientific, Ltd., Chershire, UK).

The fluorochemical acid fluorides (used for preparing the fluoro- and perfluorovinyl ethers) can be prepared from, for example, the corresponding hydrocarbon acid fluorides or acid chlorides (the latter of which are commercially available) or certain lactones, anhydrides, or esters by electrochemical fluorination in anhydrous hydrogen fluoride or by direct fluorination using elemental fluorine. Suitable fluorochemical acid fluorides include those having no hydrogen atoms bonded to the carbon atom adjacent to the carbonyl moiety. Representative examples of such fluorochemical acid fluorides include
CF$_3$C(O)F, CF$_3$CF$_2$C(O)F, CF$_3$CF$_2$CF$_2$C(O)F, (CF$_3$)$_2$CFC(O)F, C$_4$F$_9$C(O)F, CF$_3$OCF$_2$CF$_2$C(O)F, HCF$_2$CF$_2$C(O)F, CH$_3$OCF$_2$CF$_2$C(O)F, FC(O)C$_2$F$_4$C(O)F, FC(O)C$_3$F$_6$C(O)F,

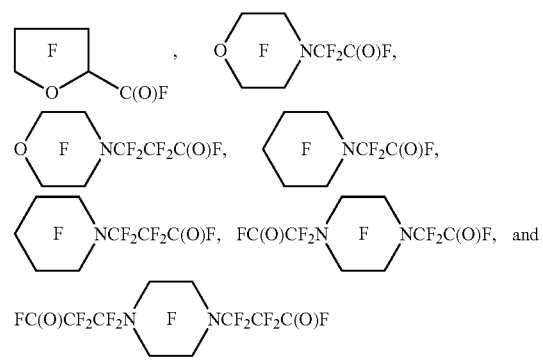

and mixtures thereof. Perfluorinated acid fluorides are typically employed from a cost and availability perspective.

Representative examples of fluoro- and perfluorovinyl ethers that are useful in preparing the provided partially fluorinated ketone compounds include C$_3$F$_7$OCF=CF$_2$, C$_3$F$_7$OCF(CF$_3$)CF$_2$OCF=CF$_2$, CF$_3$OCF=CF$_2$, C$_4$F$_9$OCF=CF$_2$, CF$_3$OC$_3$F$_6$OCF=CF$_2$, C$_2$F$_5$OCF=CF$_2$, (CF$_3$)$_2$CFCF$_2$OCF=CF$_2$, C$_5$F$_{11}$OCF=CF$_2$, HCF$_2$CF$_2$CF$_2$OCF=CF$_2$, CH$_3$OCF$_2$CF$_2$CF$_2$OCF=CF$_2$,

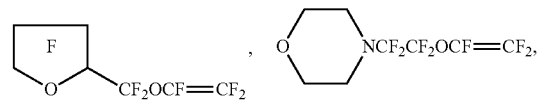

CF$_2$=CFOC$_4$F$_8$OCF=CF$_2$, and mixtures thereof. Preferred vinyl ethers include C$_3$F$_7$OCF=CF$_2$, C$_4$F$_9$OCF=CF$_2$, CF$_3$OC$_3$F$_6$OCF=CF$_2$, CF$_3$OCF=CF$_2$, C$_3$F$_7$OCF(CF$_3$)CF$_2$OCF=CF$_2$, CF$_2$=CFOC$_4$F$_8$OCF=CF$_2$ and mixtures thereof. C$_3$F$_7$OCF=CF$_2$, C$_4$F$_9$OCF=CF$_2$, and mixtures thereof are more preferred. (Mixtures of starting compounds can be used, if desired, but mixtures are generally less preferred due to the resulting production of product mixtures that can require purification.)

Suitable solvents include anhydrous, polar, aprotic solvents such as glycol ether solvents (for example, glyme, diglyme, triglyme, tetraglyme, and the like, and mixtures thereof), tetrahydrofuran, dimethylformamide, dimethyl sulfoxide, sulfolane, acetonitrile, and the like, and mixtures thereof. Typical solvents include glyme, diglyme, triglyme, tetraglyme, dimethylformamide, and mixtures thereof; with glyme, diglyme, dimethylformamide, and mixtures thereof being especially preferred.

In preparing the provided partially fluorinated ketone compounds, an alkyl aldehyde, a perfluorinated vinyl ether, and, optionally, a solvent can be combined in any order in any suitable reactor (for example, a metal reactor; typically, a pressure reactor such as a Parr reactor). The reactor can then be sealed and heated to a desired reaction temperature (for example, about 70-80° C., or even 100-150° C.) under autogenous pressure for a period sufficient to achieve a desired level of conversion (for example, for about 16-72 hours), generally with stirring or agitation of the reactor contents and, preferably, with temperature control.

After the reaction has run to completion, the reactor can be cooled and vented and the contents purified by any suitable separation method. For example, the resulting reaction mixture can be filtered, phase separated (for example, to remove the solvent and catalyst), washed with a washing solvent (for example, washed with acetone to remove residual solvent and catalyst), phase separated (for example, to remove the washing solvent), and subjected to rotary evaporation and/or distillation (for example, to remove any residual volatile materials and to purify the resulting partially fluorinated ketone product). In some embodiments, the product can be fractionally distilled directly from the reaction mixture.

The provided partially fluorinated ketone compounds (or a normally liquid composition comprising, consisting, or consisting essentially thereof) can be used in various applications. For example, the compounds can be used as solvents for precision or metal cleaning of electronic articles such as disks or circuit boards; as heat transfer agents (for example, for hybrid vehicle cooling and for the cooling or heating of integrated circuit tools in the semiconductor industry, including tools such as dry etchers, integrated circuit testers, photolithography exposure tools (steppers), ashers, chemical vapor deposition equipment, automated test equipment (probers), and physical vapor deposition equipment (sputterers); as cell size regulators in making foam insulation (for example, polyurethane, phenolic, and thermoplastic foams); as carrier fluids or solvents for document preservation materials and for lubricants; as power cycle working fluids such as for heat pumps; as heat recovery fluids in Rankine cycle engines; as inert media for polymerization reactions; as buffing abrasive agents to remove buffing abrasive compounds from polished surfaces such as metal; as displacement drying agents for removing water, such as from jewelry or metal parts; as resist developers in conventional circuit manufacturing techniques including chlorine-type developing agents; and as strippers for photoresists when used with, for example, a chlorohydrocarbon such as 1,1,1-trichloroethane or trichloroethylene.

The provided partially fluorinated ketone compounds can exhibit high dielectric strengths (for example, greater than about $10^8$ ohm-cm), which can make them well-suited for use in the semiconductor industry. Partially fluorinated ketone compounds can exhibit unexpectedly high thermal stabilities and can be particularly useful in high temperature applications such as in heat transfer applications in the semiconductor industry and in flat screen panel manufacture, and the partially fluorinated ketone compounds that have boiling points above 100° C., as well as good low temperature viscosity characteristics, are particularly useful in applications that require cycling between high temperature and low temperature heat sinks.

The provided partially fluorinated ketone compounds can be used alone or in admixture with each other or with other commonly-used solvents (for example, alcohols, ethers, alkanes, alkenes, perfluorocarbons, perfluorinated tertiary amines, perfluoroethers, cycloalkanes, esters, ketones, aromatics, siloxanes, hydrochlorocarbons, chlorinated alkenes, hydrochlorofluorocarbons, hydrofluorocarbons, and mixtures thereof). Such co-solvents can be chosen to modify or enhance the properties of a composition for a particular use and can be utilized in ratios (of co-solvent(s) to partially fluorinated ketone(s)) such that the resulting composition preferably has no flash point. If desired, the partially fluorinated ketone compounds can be used alone or in combination with other provided partially fluorinated ketone compounds.

Minor amounts of optional components can be added to the compounds to impart particular desired properties for particular uses. Useful compositions can comprise conventional additives such as, for example, surfactants, coloring agents, stabilizers, anti-oxidants, flame retardants, and the like, and mixtures thereof.

The partially fluorinated ketone compounds are useful as solvents for cleaning and drying applications such as, for example, those described in U.S. Pat. No. 5,125,089 (Flynn et al.), U.S. Pat. No. 3,903,012 (Brandreth), U.S. Pat. No. 4,169,807 (Zuber), and U.S. Pat. No. 5,925,611 (Flynn et al.) Both organic and inorganic substrates can be cleaned by contacting them with a composition comprising at least one partially fluorinated ketone of the invention. Most contaminants can be removed, including hydrocarbon contaminants, fluorocarbon contaminants, particulates, and water.

In using partially fluorinated ketone compounds for the drying of or displacing water from the surface of articles (such as circuit boards), the process of drying or water displacement described in, for example, U.S. Pat. No. 5,125,978 (Flynn et al.) can be used. Broadly, such process comprises contacting the surface of an article with a liquid composition comprising at least one partially fluorinated ketone compound of the invention, typically in admixture with a non-ionic fluoroaliphatic surface active agent. The wet article is immersed in the liquid composition and agitated therein, the displaced water is separated from the liquid composition, and the resulting water-free article is removed from the liquid composition. Further description of the process and the articles that can be treated can be found in said U.S. Pat. No. 5,125,978.

In using the provided partially fluorinated ketones as cell size regulators in making plastic foam (such as foamed polyurethane), the process reactants and reaction conditions described in, for example, U.S. Pat. No. 5,210,106 (Dams et al.) and U.S. Pat. No. 5,539,008 (Dams et al.) can be used. One such process comprises vaporizing a blowing agent mixture in the presence of at least one foamable polymer or the precursors of at least one foamable polymer, the blowing agent mixture comprising at least one provided partially fluorinated ketone.

In using the provided partially fluorinated ketones as heat transfer agents, the processes described in, for example, U.S. Reissue Pat. No. 37,119 E (Sherwood) and U.S. Pat. No. 6,374,907 (Tousignant et al.) can be used. In carrying out such processes, heat is transferred between a heat source (for example, a silicon wafer or a component of a flat panel display) and a heat sink through the use of a heat transfer agent comprising at least one provided partially fluorinated ketone compound. The provided partially fluorinated ketones are not mixtures of components of widely disparate molecular weights. Rather, the partially fluorinated ketones are generally monodisperse (that is, of a single molecular weight). This means that their physical properties remain relatively constant over time, thereby avoiding significant heat transfer performance deterioration. In addition, the provided partially fluorinated ketones generally exhibit a wide liquid range, useful viscosity over that range, and relatively high thermal stability at end use temperatures, making them well-suited for use as heat transfer fluids.

In using the provided partially fluorinated ketone compounds as deposition solvents in coating applications or in document preservation applications, the processes described in, for example, U.S. Pat. No. 5,925,611 (Flynn et al.) and U.S. Pat. No. 6,080,448 (Leiner et al.) can be used. Such processes for depositing a coating on a substrate (for example, magnetic recording media or cellulose-based materials) comprises applying, to at least a portion of at least one surface of the substrate, a composition comprising (a) a solvent composition comprising at least one provided partially fluorinated ketone compound; and (b) at least one coating material that is soluble or dispersible in the solvent composition. Coating materials that can be deposited by the process include pigments, lubricants, stabilizers, adhesives, anti-oxidants, dyes, polymers, pharmaceuticals, release agents, inorganic oxides, document preservation materials (for example, alkaline materials used in the deacidification of paper), and the like, and combinations thereof. Typical materials include perfluoropolyether, hydrocarbon, and silicone lubricants; amorphous copolymers of tetrafluoroethylene; polytetrafluoroethylene; document preservation materials; and combinations thereof. In some other useful embodiments, the material is a perfluoropolyether lubricant or a document preservation material.

In using the provided partially fluorinated ketone compounds in cutting or abrasive working operations, the processes described in, for example, U.S. Pat. No. 6,759,374 (Milbrath et al.) can be used. Such a process for metal, cermet, or composite working comprises applying a working fluid to a metal, cermet, or composite workpiece and tool, the working fluid comprising at least one provided partially fluorinated ketone compound and at least one lubricious additive. The working fluid can further comprise one or more conventional additives (for example, corrosion inhibitors, antioxidants, defoamers, dyes, bactericides, freezing point depressants, metal deactivators, co-solvents, and the like, and mixtures thereof).

In using the provided partially fluorinated ketone compounds as polymerization media, the processes described in, for example, *Research Disclosures*, Number 40576, page 81 (January 1998) and in U.S. Pat. No. 5,182,342 (Feiring et al.) and U.S. Pat. No. 6,399,729 (Farnham et al.) can be used. Such processes comprise polymerizing at least one monomer (preferably, at least one fluorine-containing monomer) in the presence of at least one polymerization initiator and at least one provided partially fluorinated ketone compound.

Objects and advantages of this invention are further illustrated by the following examples, but the particular materials and amounts thereof recited in these examples, as well as other conditions and details, should not be construed to unduly limit this invention.

EXAMPLES

Example 1

Preparation of 3,3,4-trifluoro-4-(1,1,2,2,3,3,4,4,4-nonafluorobutoxy)butan-2-one $CH_3C(O)$ $CF_2CFHOC_4F_9$ 1,1,1,2,2,3,3,4,4-nonafluoro-4-(1,2,2-trifluorovinyloxy) butane (180 g, 0.57 mol) which can be prepared by the methods described in U.S. Pat. App. Publ. No. 2008/0139683 (Flynn et al.) was combined with acetaldehyde (50.17 g, 1.14 mol, Sigma-Aldrich, St. Louis, Mo.) and t-amylperoxy-2-ethylhexanoate (4 g, 0.017 mol, United Initiators, Pullach, Germany) in a 600 mL Parr pressure reactor. The mix was heated to 75° C. for 18 hours. The reaction mix was then analyzed by GC-FID which indicated a reaction conversion of at least 64% to the product. GC/MS analysis of the crude product confirmed the desired product mass was present as the major component. The product was purified by fractional distillation to a purity of 99.4%. The boiling point of the product was 130° C. at atmospheric pressure.

Example 2

Preparation of 3,3,4-trifluoro-4-[1,1,2,2,3,3-hexafluoro-3-(2,2,3,3,5,5,6,6-octafluoromorpholin-4-yl)propoxy]butan-2-one

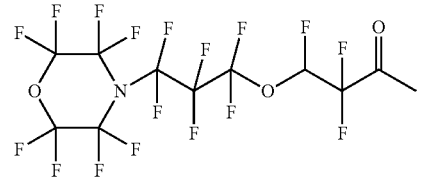 [SMILES: CC(=O)C(F)(F)C(F)OC(F)(F)C(F)(F)C(F)(F)N1C(F)(F)C(F)(F)OC(F)(F)C1(F)F]

The Michael addition reaction of methyl acrylate and morpholine was performed to generate the methyl 3-morpholinopropanoate. This organic ester was converted to the perfluorinated acyl fluoride by electrochemical fluorination (ECF) in a Simons ECF cell of essentially the type described in U.S. Pat. No. 2,713,593 (Brice et al.) and in R. E. Banks, *Preparation, Properties and Industrial Applications of Organofluorine Compounds*, pages 19-43, Halsted Press, New York (1982) to produce 2,2,3,3-tetrafluoro-3-(2,2,3,3, 5,5,6,6-octafluoromorpholin-4-yl)propanoyl fluoride.

Hexafluoropropene oxide (HFPO) (89.6 g, 0.54 mol, 3M Company) was added to the acyl fluoride (205 g, 0.54 mol) in a solution of diglyme solvent (56 g) and potassium fluoride (4 g 0.069 mol, Aldrich) in a 600 mL Parr pressure reactor. The reactor temperature was kept below 16° C. and the pressure of the HFPO was kept at or below 69 kPa during the addition. Once the HFPO addition was complete the reactor contents were emptied. Analysis by GC-FID revealed that 76% of this recovered amount was the mono-addition product and 8.8% was the di-adduct. The mono adduct was then separated from the di-adduct by fractional distillation. 2,3,3,3-tetrafluoro-2-[1,1,2,2,3,3-hexafluoro-3-(2,2,3,3,5,5,6,6-octafluoromorpholin-4-yl)propoxy]propanoyl fluoride (270 g, 0.49 mol) was combined with oven dried sodium carbonate (103 g, 0.98 mol, Aldrich) and anhydrous diglyme (400 g, Aldrich) via an addition funnel at 75° C. in a 2 L round bottom flask equipped with overhead stirring, heating mantle, thermocouple and a cold water condenser. The mix was kept dry with a nitrogen bubbler. The mixture was stirred for 18 hours at 75° C. A one-plate distillation column was put in place of the reflux line and the product was distilled from the mixture by gradually heating to 150° C. Approximately 123 g of the vinyl ether 2,2,3,3, 5,5,6,6-octafluoro-4-[1,1,2,2,3,3-hexafluoro-3-(1,2,2-trifluorovinyloxy)propyl]morpholine was recovered from this distillation. 2,2,3,3,5,5,6,6-octafluoro-4-[1,1,2,2,3,3-hexafluoro-3-(1,2,2-trifluorovinyloxy)propyl]morpholine (123 g 0.26 mol) was combined with acetaldehyde (23 g, 0.52 mol, Aldrich) and t-amylperoxy-2-ethyl hexanoate (5 g, United Initiators) in a 600 mL Parr pressure reactor. The reactor was sealed and heated to 75° C. for 18 hours. The reaction mixture was then emptied and analyzed by GC/MS which confirmed that the major component was 3,3,4-trifluoro-4-[1,1,2,2,3,3-hexafluoro-3-(2,2,3,3,5,5,6,6-octafluoromorpholin-4-yl)propoxy]butan-2-one.

Example 3

Preparation of 3,3,4-trifluoro-4-[1,1,2,2,3,3,4,4-octafluoro-4-(1,2,2-trifluoro-3-oxo-butoxy)butoxy]butan-2-one

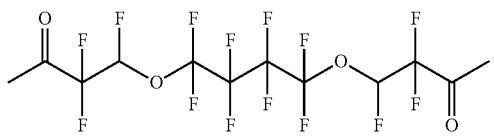 [SMILES: CC(=O)C(F)(F)C(F)OC(F)(F)C(F)(F)C(F)(F)C(F)(F)OC(F)C(F)(F)C(C)=O]

Preparation of 1,1,2,2,3,3,4,4-octafluoro-1,4-bis(1,2,2-trifluorovinyloxy)butane Unless otherwise noted, all solvents and reagents were obtained from Aldrich Chemical Co. of Milwaukee, Wis.

Preparation of Tetrafluorosuccinyl Fluoride

Tetrafluorosuccinyl fluoride was prepared by electrochemical fluorination of butyrolactone in a Simons ECF cell of the type described in U.S. Pat. No. 2,713,593 (Brice et al.) and in R. E. Banks, *Preparation and Industrial Applications of Organofluorine Compounds*, 19-43 (1982). The gaseous products from the cell were further purified by fractional distillation to yield 83% tetrafluorosuccinyl fluoride, 2% tetrafluoromethylmalonyl fluoride, 7% 3-trifluoromethoxytetrafluoropropionyl fluoride and the remainder being perfluorinated inert materials. This mixture could be used in subsequent reactions without further purification. As used herein, the term "perfluorosuccinyl fluoride" will refer to the mixture of tetrafluorosuccinyl fluoride, tetrafluoromethylmalonyl fluoride and 3-trifluoromethoxytetrafluoropropionyl fluoride just described.

Preparation of HFPO Adducts of perfluorosuccinyl fluoride, FOC(CF3)CF[OCF2(CF3)CF]mOCF2CF2CF2CF2O[CF(CF3)CF2O]nCF(CF3)COF A 600 ml stainless steel jacketed Parr pressure reactor was charged with spray-dried potassium fluoride (1.6 grams, 0.027 moles) and anhydrous diglyme (27.0 grams). The vessel was sealed, cooled to −25° C., charge with perfluorosuccinyl fluoride (200 grams, 0.934 moles) and warmed to and controlled at 13° C. Hexafluoropropene oxide (570 grams, 3.43 moles) was added over a 27 hour period with a fairly constant addition rate. The mixture was allowed to react for an additional hour and 790 grams of lower product phase was collected with the following composition.

TABLE 1

Composition of HFPO Adducts of Perfluorosuccinyl Fluoride

| m + n | GC Area % |
| --- | --- |
| 0 | 11 |
| 1 | 45 |
| 2 | 26 |

Preparation of di-vinyl ether, $CF_2=CF[OCF_2(CF_3)CF]_mOCF_2CF_2CF_2CF_2O[CF(CF_3)CF_2O]_nCF=CF_2$ m+n=0-2

A 1 L round bottom flask equipped with agitation, heating mantle, thermocouple temperature control, 100 ml barret trap and condenser connected to a nitrogen bubbler was charged with anhydrous sodium carbonate (85 grams, 0.80 moles) and anhydrous diglyme (236 grams). The vessel was heated to distill out 95 grams of wet diglyme. The reactor was cooled to 75° C. and 230 gram of HFPO adduct was charged over a 15 minute period. Following a 1 hour hold at 110° C., distillate was collected when the batch was heated to 158° C. A water wash yielded 105 grams of product containing the following components.

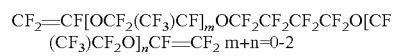

TABLE 2

Composition of Divinyl Ether

| m + n | GC Area % |
| --- | --- |
| 0 | 6 |
| 1 | 26 |
| 2 | 15 |

In a 600 mL Parr pressure reactor, 1,1,2,2,3,3,4,4-octafluoro-1,4-bis(1,2,2-trifluorovinyloxy)butane (18 g, m+n=0) was combined with 119 g of acetaldehyde and 6 g of -amylperoxy-2-ethyl hexanoate. The mixture was heated to 75° C. for 18 hours after which the reactor contents were emptied and analyzed by GC/MS. This analysis confirmed that the major component was the desired 3,3,4-trifluoro-4-[1,1,2,2,3,3,4,4-octafluoro-4-(1,2,2-trifluoro-3-oxo-butoxy)butoxy]butan-2-one.

Example 4

Preparation of 3,3,4-trifluoro-4-(1,1,2,3,3,3-hexafluoro-2-heptafluoropropyloxy-propoxy)-butan-2-one

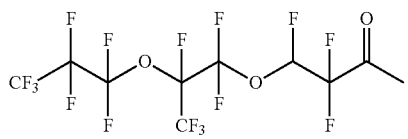 [SMILES: CC(=O)C(F)(F)C(F)OC(F)(F)C(F)(OC(F)(F)C(F)(F)C(F)(F)F)C(F)(F)F]

1,1,1,2,2,3,3-heptafluoro-3-(1,2,2-trifluoro-1-trifluoromethyl-2-trifluorovinyloxy-ethoxy)-propane, (208 grams, 0.481 moles), acetaldehyde (43.6 grams, 0.991 moles), benzoyl peroxide (1.0 g, 0.004 moles) were charged to a 600 ml Parr reactor. The reactor was cooled in dry ice and vacuum was pulled using a water aspirator. The reactor was heated to 80 C. and stirred for 16 hours. The pressure rose to a maximum of 80 psig and dropped to 172 kPa at the end of the 16 hours. The reactor was cooled to room temperature and excess pressure vented. The reactor contents were fractionated using a 10-plate Oldershaw column to obtain 143.6 grams of 3,3,4-trifluoro-4-(1,1,2,3,3,3-hexafluoro-2-heptafluoropropyloxy-propoxy)-butan-2-one with a purity of 99.4%. Structure was confirmed by g.c./m.s. Boiling Point is 156° C.

Following are exemplary embodiments of partially fluorinated ketones and methods of making and using same according to aspects of the present invention.

Embodiment 1 is a partially fluorinated ketone compound comprising: a terminal alkyl group having between 1 to 6 carbon atoms bonded to a carbonyl group to which is bonded a partially fluorinated hydrocarbon moiety, wherein the partially fluorinated hydrocarbon moiety has from 2 to 4 carbon atoms and contains at least one hydrogen substituent, an ether oxygen bonded to a carbon atom that is at least two carbon atoms removed from the carbonyl group; and a fluorinated alkyl group, having from 1 to 10 carbon atoms, bonded to the ether oxygen of the partially fluorinated hydrocarbon moiety,
wherein the fluorinated alkyl group may contain at least one catenated oxygen or nitrogen atom.

Embodiment 2 is a partially fluorinated ketone compound according to embodiment 1, wherein the terminal alkyl group is linear, branched, cyclic, or a combination thereof.

Embodiment 3 is a partially fluorinated ketone compound according to embodiment 2, wherein the terminal alkyl group is linear.

Embodiment 4 is a partially fluorinated ketone compound according to embodiment 3 wherein the terminal alkyl group is ethyl or methyl.

Embodiment 5 is a partially fluorinated ketone compound according to embodiment 1, wherein the partially fluorinated hydrocarbon moiety comprises (—$CF_2CFH$—) with the (—$CF_2$—) bonded to the carbonyl group.

Embodiment 6 is a partially fluorinated ketone compound according to embodiment 1, wherein the fluorinated alkyl group is perfluorinated.

Embodiment 7 is a partially fluorinated ketone compound according to embodiment 1, comprising two terminal alkyl groups, two partially fluorinated hydrocarbon moieties, and a fluorinated alkylene group, wherein both partially fluorinated hydrocarbon moieties are directly bonded to the fluorinated alkyl group, and wherein each partially fluorinated hydrocarbon moiety is bonded to one terminal alkyl group.

Embodiment 8 is a partially fluorinated ketone compound according to embodiment 1, wherein the partially fluorinated ketone compound is selected from the group consisting of $C_3F_7OCFHCF_2C(O)CH_3$, $C_3F_7OCF(CF_3)CF_2OCFHCF_2(O)CH_3$, $CF_3OCFHCF_2C(O)CH_3$, $C_4F_9OCFHCF_2C(O)CH_3$, $CF_3OC_3F_6OCFHCF_2C(O)CH_3$, $C_2F_5OCFHCF_2C(O)CH_3$, $(CF_3)_2CFCF_2OCFHCF_2C(O)CH_3$, $C_5F_{11}OCFHCF_2C(O)CH_3$, $HCF_2CF_2CF_2OCFHCF_2C(O)CH_3$, $CH_3OCF_2CF_2CF_2OCFHCF_2C(O)CH_3$,

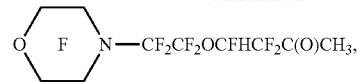

$CH_3C(O)CF_2CFHOC_4F_8OCFHCF_2C(O)CH_3$, $C_3F_7OCFHCF_2C(O)CH_2CH_3$, $C_3F_7OCFHCF_2C(O)CH_2CH_2CH_3$, $C_3F_7OCFHCF_2C(O)CH(CH_3)_2$, $C_4F_9OCFHCF_2C(O)CH_2CH_3$, $C_4F_9OCFHCF_2C(O)CH_2CH_2CH_3$, $C_4F_9OCFHCF_2C(O)CH(CH_3)_2$, $CF_3OC_3F_6OCFHCF_2C(O)CH_2CH_3$, $CF_3OC_3F_6OCFHCF_2C(O)CH_2CH_2CH_3$, $CF_3OC_3F_6OCFHCF_2C(O)CH(CH_3)_2$, $CF_3OCFHCF_2C(O)CH_2CH_3$, $CF_3OCFHCF_2C(O)CH_2CH_2CH_3$, $CF_3OCFHCF_2C(O)CH(CH_3)_2$, $C_3F_7OCF(CF_3)CF_2OCFHCF_2C(O)CH_2CH_3$, $C_3F_7OCF(CF_3)CF_2OCFHCF_2C(O)CH_2CH_2CH_3$, $C_3F_7OCF(CF_3)CF_2OCFHCF_2C(O)CH(CH_3)_2$, $CH_3CH_2(O)CCF2CFHOC_4F_8OCFHCF_2C(O)CH_2CH_3$, $CH_3CH_2CH_2C(O)CF_2CFHOC_4F_8OCFHCF_2C(O)CH_2CH_2CH_3$, $(CH_3)_2CH(O)CCF_2CFHOC_4F_8OCFHCF_2C(O)CH(CH_3)_2$,

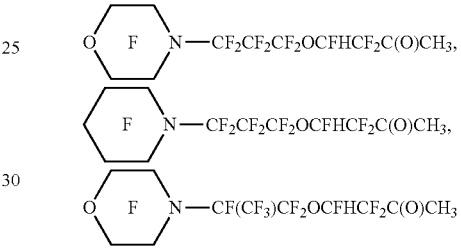

and mixtures thereof.

Embodiment 9 is a partially fluorinated ketone having the formula:

$$R_HC(=O)CF_2CFHOR_f,$$

or $$R_H^1C(=O)CF_2CFHOR_fOCFHCF_2C(=O)R_H^2$$

wherein each $R_H$, $R_H^1$, and $R_H^2$ is, independently, an alkyl group having from 1 to 4 carbon atoms, and wherein $R_f$ is a fluorinated alkyl moiety having from 1 to 6 carbon atoms.

Embodiment 10 is a partially fluorinated ketone according to embodiment 9, wherein each $R_H$, $R_H^1$, and $R_H^2$ is, independently, linear, branched, cyclic, or a combination thereof.

Embodiment 11 is a partially fluorinated ketone according to embodiment 10, wherein each $R_H$, $R_H^1$, and $R_H^2$ is, independently, linear.

Embodiment 12 is a partially fluorinated ketone according to embodiment 11, wherein each $R_H$, $R_H^1$, and $R_H^2$ is, independently, ethyl or methyl.

Embodiment 13 is a partially fluorinated ketone according to embodiment 11, wherein $R_f$ is perfluorinated.

Embodiment 14 is a partially fluorinated ketone according to embodiment 11, wherein at least one of $R_H$, $R_H^1$, $R_H^2$ and, $R_f$ comprise at least one catenated nitrogen or oxygen atom.

Embodiment 15 is a partially fluorinated ketone according to embodiment 11, wherein $R_H$ is methyl and $R_f$ is selected from:

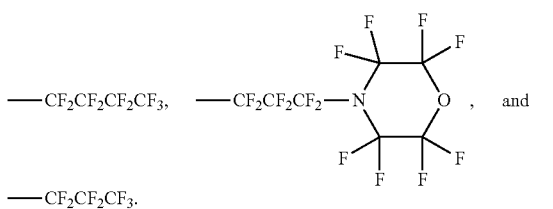

Embodiment 16 is a partially fluorinated ketone according to embodiment 11, wherein $R_H^1$ and $R_H^2$ are each methyl and $R_f$ is —$CF_2CF_2CF_2CF_2$—.

Embodiment 17 is a process for removing a contaminant from an article comprising contacting said article with a composition comprising at least one partially fluorinated ketone compound of embodiment 1.

Embodiment 18 is a process for preparing a foamed plastic comprising vaporizing a blowing agent mixture in the presence of at least one foamable polymer or the precursors of at least one foamable polymer, said blowing agent mixture comprising at least one partially fluorinated ketone compound of embodiment 1.

Embodiment 19 is a process for transferring heat comprising transferring heat between a heat source and a heat sink through the use of a heat transfer agent comprising at least one partially fluorinated ketone compound of embodiment 1.

Embodiment 20 is a process for depositing a coating on a substrate comprising: applying to at least a portion of at least one surface of said substrate a composition comprising (a) a solvent composition comprising at least partially fluorinated ketone compound of embodiment 1 and (b) at least one coating material that is soluble or dispersible in said solvent composition.

Embodiment 21 is a polymerization process comprising polymerizing at least one monomer in the presence of at least one polymerization initiator and at least one partially fluorinated ketone compound of embodiment 1.

Embodiment 22 is a method for preparing partially fluorinated ketones comprising: reacting an alkyl aldehyde having an alkyl group comprising from 2 to 6 carbon atoms with a perfluorinated vinyl ether using a free-radical initiator to form at least one partially fluorinated ketone, wherein the perfluorinated vinyl ether comprises a partially fluorinated hydrocarbon moiety, having from 2 to 4 carbon atoms, containing at least one hydrogen substituent, bonded to the carbonyl group with a carbon-carbon bond, and an ether oxygen that is at least two carbon atoms removed carbonyl group; and a fluorinated alkyl group, having from 1 to 10 carbon atoms, bonded to the ether oxygen of the partially fluorinated hydrocarbon moiety, and wherein the fluorinated alkyl group may contain at least one catenated oxygen or nitrogen atom.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows. All references cited in this disclosure are herein incorporated by reference in their entirety.

What is claimed is:

1. A partially fluorinated ketone having the formula:

$R_HC(=O)CF_2CFHOR_f$ or $R_H^1C(=O)CF_2CFHOR_fOCFHCF_2C(=O)R_H^2$ wherein each $R_H$, $R_H^1$, and $R_H^2$ is, independently, a terminal alkyl group having from 1 to 4 carbon atoms, and wherein $R_f$ is a fluorinated alkyl moiety having from 1 to 6 carbon atoms.

2. The partially fluorinated ketone according to claim 1, wherein each $R_H$, $R_H^1$, and $R_H^2$ is, independently, linear, branched, cyclic, or a combination thereof.

3. The partially fluorinated ketone according to claim 2, wherein each $R_H$, $R_H^1$, and $R_H^2$ is, independently, linear.

4. The partially fluorinated ketone according to claim 3, wherein each $R_H$, $R_H^1$, and $R_H^2$ is, independently, ethyl or methyl.

5. The partially fluorinated ketone according to claim 3, wherein $R_f$ is perfluorinated.

6. The partially fluorinated ketone according to claim 3, wherein at least one of $R_H$, $R_H^1$, $R_H^2$ and, $R_f$, comprise at least one catenated nitrogen or oxygen atom.

7. The partially fluorinated ketone according to claim 3, wherein $R_H$ is methyl and $R_f$ is selected from:

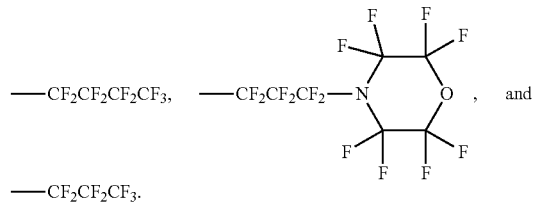

8. The partially fluorinated ketone according to claim 3, wherein $R_H^1$ and $R_H^2$ are each methyl and $R_f$ is —$CF_2CF_2CF_2CF_2$—.

9. A process for removing a contaminant from an article comprising contacting said article with a composition comprising at least one partially fluorinated ketone compound of claim 1.

10. A process for preparing a foamed plastic comprising vaporizing a blowing agent mixture in the presence of at least one foamable polymer or the precursors of at least one foamable polymer, said blowing agent mixture comprising at least one partially fluorinated ketone compound of claim 1.

11. A process for transferring heat comprising transferring heat between a heat source and a heat sink through the use of a heat transfer agent comprising at least one partially fluorinated ketone compound of claim 1.

12. A process for depositing a coating on a substrate comprising:
applying to at least a portion of at least one surface of said substrate a composition comprising (a) a solvent composition comprising at least partially fluorinated ketone compound of claim 1 and (b) at least one coating material that is soluble or dispersible in said solvent composition.

13. A polymerization process comprising polymerizing at least one monomer in the presence of at least one polymerization initiator and at least one partially fluorinated ketone compound of claim 1.

* * * * *